United States Patent
Heuer et al.

(10) Patent No.: US 8,426,395 B2
(45) Date of Patent: *Apr. 23, 2013

(54) PREPARATIONS CONTAINING CREATINE AND IMINO SUGARS

(75) Inventors: Marvin A. Heuer, Oakville, CA (US); Michele Molino, Oakville, CA (US); Joseph MacDougall, Oakville, CA (US)

(73) Assignee: Northern Northern Innovations Holding Corp, Oakville (CA)

( * ) Notice: Subject to any disclaimer, the term of this patent is extended or adjusted under 35 U.S.C. 154(b) by 930 days.

This patent is subject to a terminal disclaimer.

(21) Appl. No.: 12/229,979

(22) Filed: Aug. 28, 2008

(65) Prior Publication Data

US 2009/0297685 A1    Dec. 3, 2009

Related U.S. Application Data

(60) Provisional application No. 61/057,539, filed on May 30, 2008, provisional application No. 61/057,521, filed on May 30, 2008, provisional application No. 61/057,509, filed on May 30, 2008, provisional application No. 61/057,489, filed on May 30, 2008, provisional application No. 61/057,469, filed on May 30, 2008.

(51) Int. Cl.
*A61K 31/33* (2006.01)
*A61K 31/435* (2006.01)

(52) U.S. Cl.
USPC .......................... 514/183; 514/277; 514/634

(58) Field of Classification Search .................. 514/188, 514/277, 634, 183
See application file for complete search history.

(56) References Cited

U.S. PATENT DOCUMENTS

| | | | |
|---|---|---|---|
| 5,561,146 A * | 10/1996 | Kim et al. ............... | 514/13.7 |
| 5,886,040 A | 3/1999 | Fang | |
| 5,973,199 A | 10/1999 | Negrisoli et al. | |
| 6,166,249 A | 12/2000 | Pischel et al. | |
| 6,211,407 B1 | 4/2001 | Thomson | |
| 6,838,562 B2 | 1/2005 | Abraham et al. | |
| 6,897,334 B2 | 5/2005 | Vennerstrom | |
| 7,109,373 B2 | 9/2006 | Boldt | |
| 2004/0029969 A1 | 2/2004 | Blatt et al. | |
| 2004/0120983 A1 | 6/2004 | Connolly | |
| 2006/0269535 A1 | 11/2006 | Naidu et al. | |

FOREIGN PATENT DOCUMENTS

WO    WO-00/40217 A1    7/2000

OTHER PUBLICATIONS

Harris RC, et al. Elevation of creatine in resting and exercised muscle of normal subjects by creatine supplementation. Clin Sci (Lond). Sep. 1992;83(3):367-74.
Greenhaff PL, et al. Effect of oral creatine supplementation on skeletal muscle phosphocreatine resynthesis. Am J Physiol. May 1994;266(5 Pt 1):E725-30.
Greenhaff PL, et al. Influence of oral creatine supplementation of muscle torque during repeated bouts on maximal voluntary exercise in man. Clin Sci (Lond). May 1993;84(5):565-71.
Olsen S, et al. Creatine supplementation augments the increase in satellite cell and myonuclei number in human skeletal muscle induced by strength training. J Physiol. Jun. 2006;573(Pt 2):525-34.
Zammit PS, et al. The Skeletal Muscle Satellite Cell: The Stem Cell That Came in From the Cold. J Histochem Cytochem. Aug. 2006; 54(11):1177-91.
Sartorelli V, et al. Molecular and cellular determinants of skeletal muscle atropy and hypertropy. Sci STKE. Jul. 2004;2004(244):re11.
Mellor R, et al. Cellular effects of deoxynojirimycin analogues: uptake, retention and inhibition of glycoshingolipid biosynthesis. Biochem J. Aug. 1, 2004:381(Pt 3):861-6.
Asano N, et al. N-containing sugars from Morus alba and their glycosidase inhibitory activities. Carbohydr Res. Jun. 17, 1994;259(2):243-55.
Yoshikuni Y, et al. inhibition of intestinal alpha-glucosidase and postprandial hyperglycemia by N-substituted moranoline derivatives. J Pharmacobiodyn. May 1988;11(5):356-62.

* cited by examiner

*Primary Examiner* — Sreeni Padmanabhan
*Assistant Examiner* — Shobha Kantamneni

(57) ABSTRACT

Compounds produced by combining imino sugars and creatine are herein disclosed. The compounds being in the form of a creatine imino sugar amides and produced by the disclosed methods; protecting the guanidine group of creatine and then activating the protected creatine with DCC and reacting it with an imino sugar, followed by removal of the guanidine protecting groups. The resulting creatine imino sugar amides have enhanced stability in solution as compared to related esters. In addition, specific benefits are conferred by the imino sugar in addition to, and separate from, the creatine substituent. Methods of preparation and use of these compounds are also disclosed.

6 Claims, No Drawings

PREPARATIONS CONTAINING CREATINE AND IMINO SUGARS

RELATED APPLICATIONS

The present application is related to and claims benefit of priority to U.S. Provisional Application No. 61/059,938 entitled "Salts of Creatine Imino Sugar Amides" filed Jun. 9, 2008, the disclosure of which is hereby fully incorporated by reference; and 61/057,539, U.S. Provisional Application No. 61/057,521, U.S. Provisional Application No. 61/057,509, U.S. Provisional Application No. 61/057,489, and U.S. Provisional Application No. 61/057,469, all of which were filed May 30, 2008, the disclosure of which are all hereby fully incorporated by reference. Additionally, the instant application is related to the applicant's co-pending U.S. patent application Ser. No. 12/229,955, entitled "Salts of Creatine Imino Sugar Amides" filed on this same day, herein fully incorporated by reference.

FIELD OF THE INVENTION

The present invention relates to structures and methods for producing creatine imino sugar amides. Specifically, the present invention relates to compounds comprising an imino sugar bound to creatine, via an amide linkage.

BACKGROUND OF THE INVENTION

Creatine is a naturally occurring amino acid that is derived from the amino acids; glycine, arginine and methionine. Although it is ingested from meats and fish, the human body also synthesizes its own creatine. About 65% of creatine is stored in the musculature of mammals in the form of phosphocreatine (creatine bound to a phosphate molecule), and utilized mostly as a source of energy for muscle. Oral supplementation of creatine has been shown to increase creatine concentration in muscle, and also enables an increase in the resynthesis of phosphocreatine, resulting in a rapid replenishment of ATP within the first two minutes of the start of exercise.

The beneficial effects of creatine supplementation with regard to skeletal muscle are apparently not restricted to the role of creatine in energy metabolism. Creatine supplementation in combination with strength training results in specific, measurable physiological changes in skeletal muscle compared to strength training alone. For example, creatine supplementation amplifies the strength training-induced increase of human skeletal satellite cells as well as the number of myonuclei in human skeletal muscle fibers. Satellite cells, stem cells of adult muscle, are normally in a quiescent state and become activated to fulfill roles of routine maintenance, repair and hypertrophy. Postnatal muscle growth involves both myofiber hypertrophy and increased numbers of myonuclei—the source of which are satellite cells.

Imino sugars constitute a major class of naturally occurring molecules that have important and diverse biological functions. Imino sugars may be pentose, hexose or heptose sugars where at least one oxygen-containing group is replaced by a nitrogen-containing group. These imino sugars are useful in pharmacology, since they have been found to play major roles in the selective inhibition of various enzymatic functions.

Many have attempted to address issues such as stability, solubility, and bioavailability of creatine and imino sugars, independently, through the use of salts, esters, and amides. However, compounds of an imino sugar and a creatine bound via an amide bond are not known. It is commonly understood that hydrolysis of amides is more difficult to accomplish than the hydrolysis of esters. Therefore, an amide of creatine and an imino sugar would be more stable in solution than the related ester.

SUMMARY OF THE INVENTION

In the present invention, compounds and methods of production are disclosed, wherein the compounds comprise an imino sugar bound to creatine, via an amide linkage, and having a structure corresponding to Formula 1:

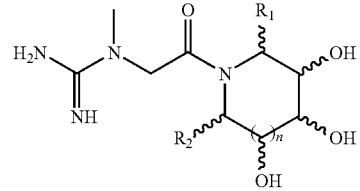

Formula 1 where
$R_1$=H, OH, or $CH_2OH$;
$R_2$=H, OH, $CH_3$ or $CH_2OH$; and
n=0, 1 or 2.

An additional aspect of the present invention discloses a method for producing the compound corresponding to Formula 1.

In a further aspect of the present invention, the compound corresponding to Formula 1 may be combined with one or more pharmaceutically acceptable carriers to form a nutritional composition, which can be orally administered to a subject.

DETAILED DESCRIPTION OF THE INVENTION

In the following description, for the purposes of explanation, numerous specific details are set forth in order to provide a thorough understanding of the present invention. It will be apparent, however, to one skilled in the art that the present invention may be practiced without these specific details.

The present invention relates to compounds of creatine imino sugar amides and their routes of syntheses. Specific benefits are conferred by the creatine portion of the compound in addition to, and separate from, the imino sugar substituent.

As used herein, 'creatine' refers to the chemical N-methyl-N-guanyl Glycine, (CAS Registry No. 57-00-1), also known as, (alpha-methyl guanido) acetic acid, N-(aminoiminomethyl)-N-glycine, Methylglycocyamine, Methylguanidoacetic Acid, or N-Methyl-N-guanylglycine. Additionally, as used herein, 'creatine' also includes derivatives of creatine such as esters and salts, as well as other derivatives, including derivatives having pharmacoproperties upon metabolism to an active form.

As used herein, 'deoxynojirimycin' refers to the chemical (2R,3R,4R,5S)-2-(hydroxymethyl)-3,4,5-piperideinetriol, (CAS Registry No. 19130-96-2), also known as D-5-amino-1,5-dideoxyglucopyranose, 1,5-dideoxy-1,5-imino-D-glucitol, (2R,3R,4R,5S)-2-hydroxymethyl-3,4,5-trihydroxypiperidine, or moranoline. Additionally, as used herein, 'deoxynojirimycin' also includes derivatives of deoxynojirimycin such as esters and salts.

As used herein, 'deoxygalactonojirimycin' refers to the chemical 2-(hydroxymethyl)piperidine-3,4,5-triol, (CAS Registry No. 75172-81-5), also known as 1,5-dideoxy-1,5-imino-D-galactitol, or galactostatin. Additionally, as used here, 'deoxygalactonojirimycin' also includes derivatives of deoxygalactonojirimycin such as esters and salts.

As used herein, 'deoxymannojirimycin' refers to the chemical (2R,3R,4R,5R)-2-(hydroxymethyl)piperidine-3,4,5-triol, (CAS Registry No. 73465-43-7), also known as 1,5-dideoxy-1,5-imino-D-mannitol. Additionally, as used here, 'deoxymannojirimycin' also includes derivatives of deoxymannojirimycin such as esters and salts.

As used herein, 'homomannojirimycin' refers to the chemical (2R,3R,5R,6R)-2,6-bis(hydroxymethyl)piperidine-3,4,5-triol, (CAS Registry No. 127995-29-3). Additionally, as used here, 'homomannojirimycin' also includes derivatives of homomannojirimycin such as esters and salts.

As used herein, 'homonojirimycin' refers to the chemical (2R,3R,5S,6R)-2,6-bis(hydroxymethyl)piperidine-3,4,5-triol, (CAS Registry No. 119557-99-2). Additionally, as used here, 'homonojirimycin' also includes derivatives of homonojirimycin such as esters and salts.

As used herein, the term 'subject' refers to mammals and non-mammals. Mammals refers to any member of the mammalia class including, but not limited to, humans; non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like.

As used here, the term 'acceptable oral dosage form' would be known by one of skill in the art to include, for example, powder beverage mixes, liquid beverages, ready-to-eat bars, capsules, liquid capsules, tablets, capleta, dietary gels, Soft-Gel™ caplets, and gel-caps.

The term 'pharmaceutically acceptable carrier' is art-recognized and refers to a pharmaceutically-acceptable material, composition or vehicle, such as a liquid or solid filler, diluent, excipient, solvent or encapsulating material, involved in carrying or transporting any subject composition or component thereof. Each carrier must be 'acceptable' in the sense of being compatible with the subject composition and its components and not injurious to the individual to which it is administered. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; and (15) other non-toxic compatible substances employed in pharmaceutical formulations, and combinations thereof.

As used herein, the term 'nutritional composition' includes dietary supplements, diet supplements, nutritional supplements, supplemental compositions and supplemental dietary compositions or those similarly envisioned and termed compositions not belonging to the conventional definition of pharmaceutical interventions as is known in the art. Furthermore, 'nutritional compositions' as disclosed herein belong to category of compositions having at least one physiological function when administered to a subject by conventional routes of administration.

Alternatively, formulations and nutritional compositions belonging to the present invention may be considered to be nutraceuticals. As used herein, the term 'nutraceutical' is recognized and used in the art to describe a specific chemical compound or combination of compounds found in, organic matter for example, which may prevent, ameliorate or otherwise confer benefits against an undesirable condition. As is known in the art, the term 'nutraceutical' is used to refer any substance that is a food, a part of food, or an extract of food which is suitable for consumption by an individual and providing physiological benefit which may be medical or health-related. Furthermore, the term has been used to refer to a product isolated, extracted or purified from foods or naturally-derived material suitable for consumption by an individual and usually sold in medicinal forms, such as caplets, tablets, capsules, Soft-Gel™ caplets, gel-caps and the like, not associated with food.

According to the present invention, the compounds disclosed herein comprise imino sugars bound to creatine. Furthermore, the imino sugars and creatine are bound by an amide linkage and have a structure according to Formula 1. The aforementioned compounds can be prepared according to the reaction as set forth for the purposes of the description in Scheme 1 below:

Scheme 1

Step 1:

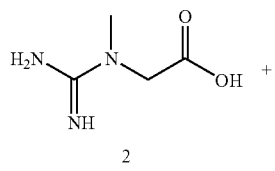

2

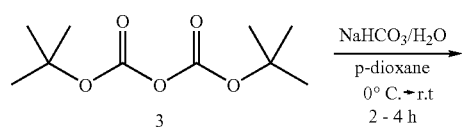

3

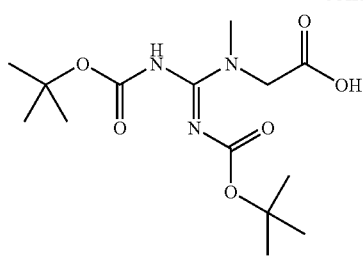
4
Step 2:
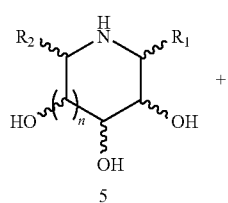
5
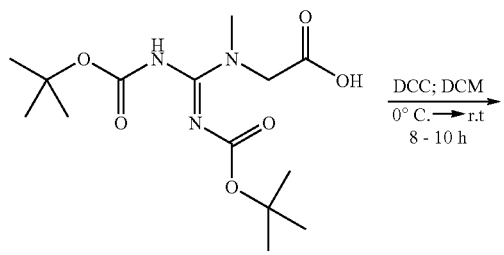
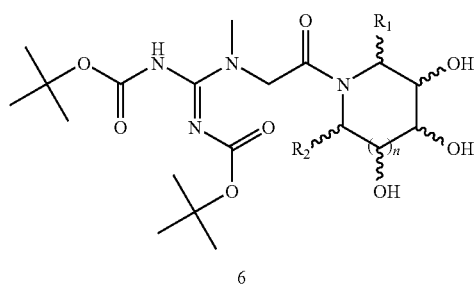
6
Step 3:
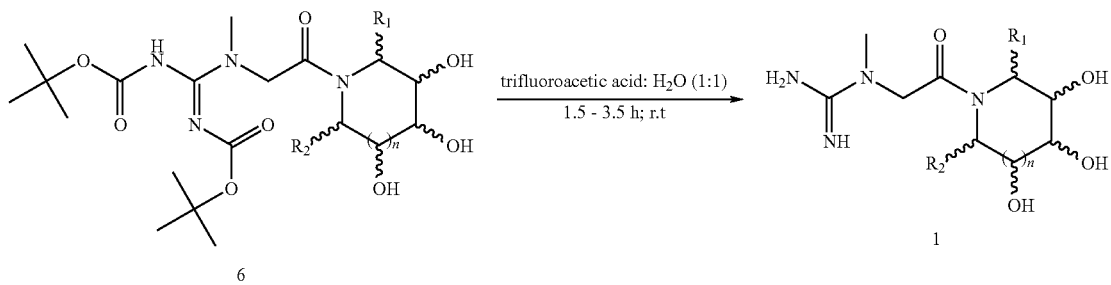
$R_1$ = H, OH, or CH$_2$OH;
$R_2$ = H, OH, CH$_3$ or CH$_2$OH;
and n = 0, 1 or 2

With reference to Scheme 1, in Step 1, creatine (2) is dissolved in water and an excess of sodium bicarbonate (NaHCO$_3$) is added with stirring and then cooled in an ice-water bath. The resultant solution is cooled in an ice-water bath and di-tert-butyl carbonate (3), also known as boc anhydride, is added as a solution in p-dioxane (also cooled). The mixture is then stirred at about 0° C. for about one hour and allowed to warm to room temperature (~23° C.) for between 2-4 hours. Water is added to the mixture and the aqueous layer is extracted twice with ethyl acetate. The resultant organic layer is then back extracted twice with a saturated sodium bicarbonate solution. The combined aqueous layers are acidified to a pH of 1 with 10% HCl and then extracted three times with ethyl acetate. The organic layers are combined, dried over sodium sulfate, filtered and concentrated in vacuo. The resultant protected creatine (4) would be of sufficient purity to be used in subsequent steps.

Step 2 describes the combining of an imino sugar (5) and the protected creatine (4). The two substrates, 5 and 4, are stirred in DCM and submersed in an ice-water bath to bring to the temperature of the reaction to about 0° C. After cooling, a solution of dicyclohexylcarbodiimine (DCC) and DCM is added to the mixture of 5 and 4 with vigorous stirring; the DCC acts to activate the carboxylic acid of the protected creatine in situ. Following the addition of the DCC the reaction is allowed to warm to room temperature (~23° C.) with constant agitation. Stirring is maintained overnight (between about 8 and about 10 hours). The mixture is then filtered through Celite® in order to remove any by-products and unreacted materials. The filtrate is then concentrated under reduced pressure and purified by flash chromatography through a silica gel packed column to yield the bis-boc-protected creatine imino sugar amide (6).

In the preferred embodiment of the present invention, deoxynojirimycin is the imino sugar used. However any imino sugar, as is known by one of skill in the art, may be utilized to synthesize a creatine imino sugar amide according to the method disclosed herein.

Step 3 describes the removal of the two boc protecting groups from the guanidine group of 6, via acidification. The bis-boc-protected creatine imino sugar amide (6) is dissolved in a trifluoroacetic acid:H$_2$O (1:1) mixture. The reaction is stirred at room temperature for between about 1.5 and about 3.5 hours. After the reaction is complete the mixture is concentrated under reduced pressure and then purified by flash chromatography through a silica gel packed column to yield the target amide, creatine imino sugar amide (1).

According to an additional embodiment, the creatine imino sugar amide of the present invention may be formulated into nutritional compositions that may be consumed in any form. For instance, the dosage form of the nutritional compositions may be provided as, e.g. a powder beverage mix, a liquid beverage, a ready-to-eat bar or drink product, a capsule, a liquid capsule, a tablet, a caplet, or as a dietary gel. The preferred dosage forms of the present invention are provided as a powder beverage mix.

Furthermore, the dosage form of the nutritional composition may be provided in accordance with customary processing techniques for herbal and nutritional compositions in any of the forms mentioned above. Additionally, the nutritional composition, comprising the creatine imino sugar amide may contain any appropriate number and type of pharmaceutically acceptable carriers, as is well known in the art.

The following non-limiting example illustrates feasible synthesis of various creatine imino sugar amides. One of skill in the art may readily envision various other combinations within the scope of the present invention, considering the example with reference to the specification herein provided.

EXAMPLE

Example 1

1-methyl-1-(2-oxo-2-((2R,3R,4R,5S)-3,4,5-trihy-droxy-2-(hydroxymethyl)piperidin-1-yl)ethyl)guanidine

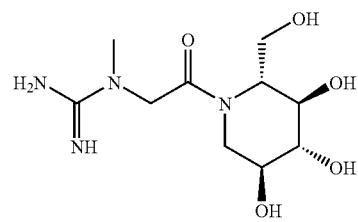 [SMILES: CN(CC(=O)N1C[C@H](O)[C@@H](O)[C@H](O)[C@H]1CO)C(=N)N]

In a round bottomed flask, equipped with a magnetic stirrer, 7.87 g (0.060 mol) of creatine is dissolved in 200 mL of water and 10.08 g (0.120 mol) of sodium bicarbonate is added with stirring. The solution is then cooled to about 0° C. in an ice-water bath. To the cooled solution is added a cooled solution of 31.10 ml (0.150 mol) of di-tert-butyl dicarbonate dissolved in 150 mL of p-dioxane. The mixture is then stirred at about 0° C. in an ice-water bath for an hour, after which the ice bath is removed and the solution is allowed to warm to room temperature (~23° C.). After stirring at room temperature for an additional 2 hours, the mixture is diluted with 150 mL of water and transferred to a 1-L separatory funnel, where the aqueous layer is extracted sequentially with one 300 mL and one 150 mL portions of ethyl acetate. The resultant organic layer is then back extracted sequentially one 150 mL and one 75 mL portions of saturated sodium bicarbonate solution. The combined aqueous portions are then slowly acidified to a pH of 1, in a 1-L separatory funnel, with 10% HCl, and then extracted with three 100 mL ethyl acetate portions. The organic layers are then combined, dried over sodium sulphate, filtered and then concentrated under reduced pressure. The resultant 2-(2,3-bis(tert-butoxycarbonyl)-1-methylguanidino)acetic acid would be sufficiently pure to use in subsequent steps.

A dry, 2-necked round bottomed flask, equipped with a magnetic stirrer and a dropping funnel containing a solution of 10.83 g (0.0525 mol) of N,N'-dicyclohexylcarbodiimide (DCC) dissolved in 125 mL of DCM, is charged with 16.57 g (0.050 mol) of 2-(2,3-bis(tert-butoxycarbonyl)-1-methylguanidino)acetic acid, 8.97 g (0.055 mol) of deoxynojirimycin, and 100 mL of DCM (all of which is under an argon atmosphere). The resultant mixture is stirred in an ice-water bath to cool the solution to a temperature of about 0° C. Following cooling, the solution of DCC from the dropping funnel is added and the reaction is allowed to warm to room temperature and then to stir overnight. The mixture is then filtered through a Celite® plug and the filtrate is purified by flash chromatography (ethyl acetate/hexanes; 1/3) to yield the bis-boc protected creatine deoxynojirimycin amide, tert-butyl(tert-butoxycarbonylamino)(methyl(2-oxo-2-((2R,3R,4R,5S)-3,4,5-trihydroxy-2-(hydroxymethyl)piperidin-1-yl)ethyl)amino)methylene-carbamate.

In a dry, round bottomed flask, equipped with a magnetic stirrer, 19.06 g (0.040 mol) of tert-butyl(tert-butoxycarbonylamino)(methyl(2-oxo-2-((2R,3R,4R,5S)-3,4,5-trihydroxy-2-(hydroxymethyl)piperidin-1-yl)ethyl)amino) methylenecarbamate is dissolved in 250 mL of a trifluoroacetic acid:H2O (1:1) mixture. The resultant mixture is stirred for 1.5 hours at room temperature, after which it is concentrated under reduced pressure and then purified by flash chromatography (ethyl acetate/hexanes; 1/5) to yield the creatine deoxynojirimycin amide, 1-methyl-1-(2-oxo-2-((2R,3R,4R,5S)-3,4,5-trihydroxy-2-(hydroxymethyl)piperidin-1-yl)ethyl) guanidine.

Example 2

1-methyl-1-(2-oxo-2-((3S,4R,5S)-3,4,5-trihydroxy-2-(hydroxymethyl)piperidin-1-yl)ethyl)guanidine

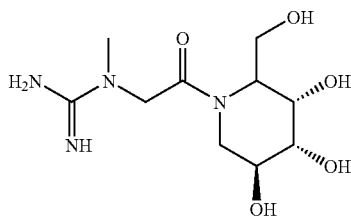 [SMILES: CN(CC(=O)N1C[C@H](O)[C@@H](O)[C@@H](O)C1CO)C(=N)N]

In a round bottomed flask, equipped with a magnetic stirrer, 6.50 g (0.050 mol) of creatine is dissolved in 175 mL of water and 8.40 g (0.10 mol) of sodium bicarbonate is added with stirring. The solution is then cooled to about 0° C. in an ice-water bath. To the cooled solution is added a cooled solution of 28.72 ml (0.10 mol) of di-tert-butyl dicarbonate dissolved in 125 mL of p-dioxane. The mixture is then stirred at 0° C. in an ice-water bath for an hour, after which the ice-water bath is removed and the solution is allowed to warm to room temperature (~23° C.). After stirring at room temperature for an additional 2 hours, the mixture is diluted with 150 mL of water and transferred to a 1-L separatory funnel, where the aqueous layer is extracted sequentially with one 300 mL and one 150 mL portions of ethyl acetate. The resultant organic layer is then back extracted sequentially one 150 mL and one 75 mL portions of saturated sodium bicarbonate solution. The combined aqueous portions are then slowly acidified to a pH of 1, in a 1-L separatory funnel, with 10% HCl, and then extracted with three 100 mL ethyl acetate portions. The organic layers are then combined, dried over sodium sulphate, filtered and then concentrated under reduced pressure. The resultant 2-(2,3-bis(tert-butoxycarbonyl)-1-methylguanidino)acetic acid would be sufficiently pure to use in subsequent steps.

A dry, 2-necked round bottomed flask, equipped with a magnetic stirrer and a dropping funnel containing a solution of 8.66 g (0.042 mol) of N,N'-dicyclohexylcarbodiimide (DCC) dissolved in 100 mL of DCM, is charged with 13.25 g (0.040 mol) of 2-(2,3-bis(tert-butoxycarbonyl)-1-methylguanidino)acetic acid, 7.18 g (0.044 mol) of deoxygalactonojirimycin, and 75 mL of DCM (all of which is under an argon atmosphere). The resultant mixture is stirred in an ice-water bath to cool the solution to a temperature of about 0° C. Following cooling, the solution of DCC from the dropping funnel is added and the reaction is allowed to warm to room temperature and then to stir overnight. The mixture is then filtered through a Celite® plug and the filtrate is purified by flash chromatography (ethyl acetate/hexanes; 1/3) to yield the bis-boc protected creatine deoxygalactonojirimycin amide, tert-butyl(tert-butoxycarbonylamino)(methyl(2-oxo-2-((3S,4R,5S)-3,4,5-trihydroxy-2-(hydroxymethyl)piperidin-1-yl)ethyl)amino)methylenecarbamate.

In a dry, round bottomed flask, equipped with a magnetic stirrer, 23.81 g (0.050 mol) of tert-butyl(tert-butoxycarbonylamino)(methyl(2-oxo-2-((3S,4R,5S)-3,4,5-trihydroxy-2-(hydroxymethyl)piperidin-1-yl)ethyl)amino)methylenecarbamate is dissolved in 275 mL of a trifluoroacetic acid:H₂O (1:1) mixture. The resultant mixture is stirred for 2 hours at room temperature, after which it is concentrated under reduced pressure and then purified by flash chromatography (ethyl acetate/hexanes; 2/3) to yield the creatine deoxygalactonojirimycin amide, 1-methyl-1-(2-oxo-2-((3S,4R,5S)-3,4,5-trihydroxy-2-(hydroxymethyl)piperidin-1-yl)ethyl)guanidine.

Example 3

1-methyl-1-(2-oxo-2-((2R,3R,4R,5R)-3,4,5-trihydroxy-2-(hydroxymethyl)piperidin-1-yl)ethyl)guanidine

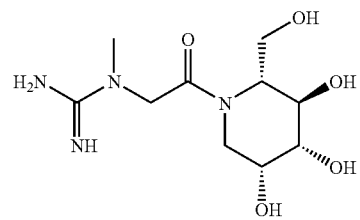 [SMILES: CN(CC(=O)N1C[C@@H](O)[C@@H](O)[C@H](O)[C@H]1CO)C(=N)N]

In a round bottomed flask, equipped with a magnetic stirrer, 9.17 g (0.070 mol) of creatine is dissolved in 300 mL of water and 11.76 g (0.140 mol) of sodium bicarbonate is added with stirring. The solution is then cooled to about 0° C. in an ice-water bath. To the cooled solution is added a cooled solution of 40.20 ml (0.175 mol) of di-tert-butyl dicarbonate dissolved in 175 mL of p-dioxane. The mixture is then stirred at about 0° C. in an ice-water bath for an hour, after which the ice-water bath is removed and the solution is allowed to warm to room temperature (~23° C.). After stirring at room temperature for an additional 3 hours, the mixture is diluted with 250 mL of water and transferred to a 2-L separatory funnel, where the aqueous layer is extracted sequentially with one 300 mL and one 150 mL portions of ethyl acetate. The resultant organic layer is then back extracted sequentially one 150 mL and one 75 mL portions of saturated sodium bicarbonate solution. The combined aqueous portions are then slowly acidified to a pH of 1, in a 2-L separatory funnel, with 10% HCl, and then extracted with three 100 mL ethyl acetate portions. The organic layers are then combined, dried over sodium sulphate, filtered and then concentrated under reduced pressure. The resultant 2-(2,3-bis(tert-butoxycarbonyl)-1-methylguanidino)acetic acid would be sufficiently pure to use in subsequent steps.

A dry, 2-necked round bottomed flask, equipped with a magnetic stirrer and a dropping funnel containing a solution of 13.00 g (0.063 mol) of N,N'-dicyclohexylcarbodiimide (DCC) dissolved in 150 mL of DCM, is charged with 19.88 g (0.060 mol) of 2-(2,3-bis(tert-butoxycarbonyl)-1-methylguanidino)acetic acid, 10.77 g (0.066 mol) of deoxymannojirimycin, and 150 mL of DCM (all of which is under an argon atmosphere). The resultant mixture is stirred in an ice-water bath to cool the solution to a temperature of about 0°

C. Following cooling, the solution of DCC from the dropping funnel is added and the reaction is allowed to warm to room temperature and then to stir overnight. The mixture is then filtered through a Celite® plug and the filtrate is purified by flash chromatography (ethyl acetate/hexanes; 1/3) to yield the bis-boc protected creatine deoxymannojirimycin amide, tert-butyl(tert-butoxycarbonylamino)(methyl(2-oxo-2-((2R,3R,4R,5R)-3,4,5-trihydroxy-2-(hydroxymethyl)piperidin-1-yl)ethyl)amino)methylenecarbamate.

In a dry, round bottomed flask, equipped with a magnetic stirrer, 30.96 g (0.065 mol) of tert-butyl(tert-butoxycarbonylamino)(methyl(2-oxo-2-((2R,3R,4R,5R)-3,4,5-trihydroxy-2-(hydroxymethyl)piperidin-1-yl)ethyl)amino)methylenecarbamate is dissolved in 325 mL of a trifluoroacetic acid:$H_2O$ (1:1) mixture. The resultant mixture is stirred for 3 hours at room temperature, after which it is concentrated under reduced pressure and then purified by flash chromatography (ethyl acetate/hexanes; 1/5) to yield the creatine deoxymannojirimycin amide, 1-methyl-1-(2-oxo-2-((2R,3R,4S,5S,6R)-3,4,5-trihydroxy-2,6-bis(hydroxymethyl)piperidin-1-yl)ethyl)guanidine.

Example 4

1-methyl-1-(2-oxo-2-((2R,3R,5R,6R)-3,4,5-trihydroxy-2,6-bis(hydroxymethyl)piperidin-1-yl)ethyl)guanidine

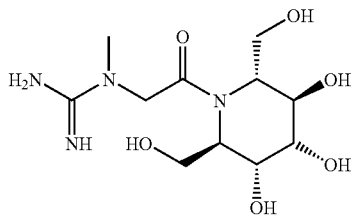

In a round bottomed flask, equipped with a magnetic stirrer, 3.93 g (0.030 mol) of creatine is dissolved in 150 mL of water and 5.04 g (0.060 mol) of sodium bicarbonate is added with stirring. The solution is then cooled to about 0° C. in an ice-water bath. To the cooled solution is added a cooled solution of 17.24 mL (0.075 mol) of di-tert-butyl dicarbonate dissolved in 100 mL of p-dioxane. The mixture is then stirred at about 0° C. in an ice-water bath for an hour, after which the ice-water bath is removed and the solution is allowed to warm to room temperature (~23° C.). After stirring at room temperature for an additional hour, the mixture is diluted with 125 mL of water and transferred to a 1-L separatory funnel, where the aqueous layer is extracted sequentially with one 200 mL and one 75 mL portions of ethyl acetate. The resultant organic layer is then back extracted sequentially one 100 mL and one 50 mL portions of saturated sodium bicarbonate solution. The combined aqueous portions are then slowly acidified to a pH of 1, in a 1-L separatory funnel, with 10% HCl, and then extracted with three 75 mL ethyl acetate portions. The organic layers are then combined, dried over sodium sulphate, filtered and then concentrated under reduced pressure. The resultant 2-(2,3-bis(tert-butoxycarbonyl)-1-methylguanidino)acetic acid would be sufficiently pure to use in subsequent steps.

A dry, 2-necked round bottomed flask, equipped with a magnetic stirrer and a dropping funnel containing a solution of 6.50 g (0.0315 mol) of N,N'-dicyclohexylcarbodiimide (DCC) dissolved in 80 mL of DCM, is charged with 9.94 g (0.030 mol) of 2-(2,3-bis(tert-butoxycarbonyl)-1-methylguanidino)acetic acid, 6.38 g (0.033 mol) of homomannojirimycin, and 100 mL of DCM (all of which is under an argon atmosphere). The resultant mixture is stirred in an ice-water bath to cool the solution to a temperature of about 0° C. Following cooling, the solution of DCC from the dropping funnel is added and the reaction is allowed to warm to room temperature and then to stir overnight. The mixture is then filtered through a Celite® plug and the filtrate is purified by flash chromatography (ethyl acetate/hexanes; 1/3) to yield the bis-boc protected creatine homomannojirimycin amide, tert-butyl(tert-butoxycarbonylamino)(methyl(2-oxo-2-((2R,3R,5R,6R)-3,4,5-trihydroxy-2,6-bis(hydroxymethyl)piperidin-1-yl)ethyl)amino)methylene-carbamate.

In a dry, round bottomed flask, equipped with a magnetic stirrer, 10.12 g (0.020 mol) of tert-butyl(tert-butoxycarbonylamino)(methyl(2-oxo-2-((2R,3R,5R,6R)-3,4,5-trihydroxy-2,6-bis(hydroxymethyl)piperidin-1-yl)ethyl)amino)methylenecarbamate is dissolved in 150 mL of a trifluoroacetic acid:$H_2O$ (1:1) mixture. The resultant mixture is stirred for 2 hours at room temperature, after which it is concentrated under reduced pressure and then purified by flash chromatography (ethyl acetate/hexanes; 1/5) to yield the creatine homomannojirimycin amide, 1-methyl-1-(2-oxo-2-((2R,3R,5R,6R)-3,4,5-trihydroxy-2,6-bis(hydroxymethyl)piperidin-1-yl)ethyl)guanidine.

Example 5

1-methyl-1-(2-oxo-2-((2R,3R,4S,5S,6R)-3,4,5-trihydroxy-2,6-bis(hydroxymethyl)piperidin-1-yl)ethyl)guanidine

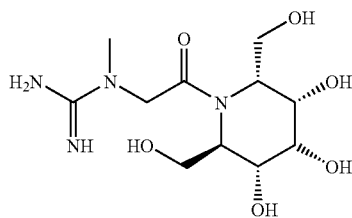

In a round bottomed flask, equipped with a magnetic stirrer, 7.87 g (0.060 mol) of creatine is dissolved in 200 mL of water and 10.08 g (0.120 mol) of sodium bicarbonate is added with stirring. The solution is then cooled to about 0° C. in an ice-water bath. To the cooled solution is added a cooled solution of 31.10 ml (0.150 mol) of di-tert-butyl dicarbonate dissolved in 150 mL of p-dioxane. The mixture is then stirred at about 0° C. in an ice-water bath for an hour, after which the ice-water bath is removed and the solution is allowed to warm to room temperature (~23° C.). After stirring at room temperature for an additional 2 hours, the mixture is diluted with 150 mL of water and transferred to a 1-L separatory funnel, where the aqueous layer is extracted sequentially with one 300 mL and one 150 mL portions of ethyl acetate. The resultant organic layer is then back extracted sequentially one 150 mL and one 75 mL portions of saturated sodium bicarbonate solution. The combined aqueous portions are then slowly acidified to a pH of 1, in a 1-L separatory funnel, with 10% HCl, and then extracted with three 100 mL ethyl acetate portions. The organic layers are then combined, dried over sodium sulphate, filtered and then concentrated under reduced pressure. The resultant 2-(2,3-bis(tert-butoxycarbonyl)-1-methylguanidino)acetic acid would be sufficiently pure to use in subsequent steps.

A dry, 2-necked round bottomed flask, equipped with a magnetic stirrer and a dropping funnel containing a solution of 10.83 g (0.0525 mol) of N,N'-dicyclohexylcarbodiimide (DCC) dissolved in 60 mL of DCM, is charged with 16.57 g (0.050 mol) of 2-(2,3-bis(tert-butoxycarbonyl)-1-methylguanidino)acetic acid, 10.62 g (0.055 mol) of homonojirimycin, and 100 mL of DCM (all of which is under an argon atmosphere). The resultant mixture is stirred in an ice-water bath to cool the solution to a temperature of about 0° C. Following cooling, the solution of DCC from the dropping funnel is added and the reaction is allowed to warm to room temperature and then to stir overnight. The mixture is then filtered through a Celite® plug and the filtrate is purified by flash chromatography (ethyl acetate/hexanes; 1/3) to yield the bis-boc protected creatine homonojirimycin amide, tert-butyl (tert-butoxycarbonylamino)(methyl(2-oxo-2-((2R,3R,4S,5S,6R)-3,4,5-trihydroxy-2,6-bis(hydroxymethyl)piperidin-1-yl)ethyl)amino)methylenecarbamate.

In a dry, round bottomed flask, equipped with a magnetic stirrer, 20.62 g (0.040 mol) of tert-butyl(tert-butoxycarbonylamino)(methyl(2-oxo-2-((2R,3R,4S,5S,6R)-3,4,5-trihydroxy-2,6-bis(hydroxymethyl)piperidin-1-yl)ethyl)amino)methylenecarbamate is dissolved in 250 mL of a trifluoroacetic acid:H$_2$O (1:1) mixture. The resultant mixture is stirred for 2 hours at room temperature, after which it is concentrated under reduced pressure and then purified by flash chromatography (ethyl acetate/hexanes; 1/5) to yield the creatine homonojirimycin amide, 1-methyl-1-(2-oxo-2-((2R,3R,4S,5S,6R)-3,4,5-trihydroxy-2,6-bis(hydroxymethyl)piperidin-1-yl)ethyl)guanidine.

EXTENSIONS AND ALTERNATIVES

In the foregoing specification, the invention has been described with respect to specific embodiments thereof; however, it will be evident to one skilled in the art that various modifications and changes may be made thereto without departing from the scope of the invention.

All publications which are cited herein are hereby specifically incorporated by reference into the disclosure for the teachings for which they are cited.

What is claimed:
1. A compound having the structure:

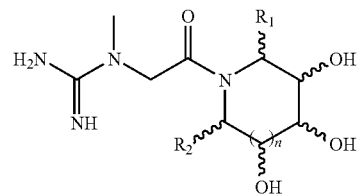

where
R$_1$=H, OH, or CH$_2$OH;
R$_2$=H, OH, CH$_3$ or CH$_2$OH; and
n=0, 1 or 2.

2. A nutritional composition comprising at least one pharmaceutically acceptable carrier or diluent and the compound of claim 1.

3. The nutritional composition of claim 2, wherein the composition is provided to a subject in an acceptable oral dosage form.

4. The composition of claim 3, wherein the subject is a mammal.

5. The nutritional composition of claim 3, wherein the acceptable oral dosage form is selected from the group consisting of a powder beverage mix, a liquid beverage, a ready-to-eat bar, a capsule, a liquid capsule, a tablet, a caplet, a dietary gel, a Soft-Gel™ caplet, and a gel-cap.

6. A compound selected from the group consisting of: 1-methyl-1-(2-oxo-2-((2R,3R,4R,5S)-3,4,5-trihydroxy-2-(hydroxymethyl)piperidin-1-yl)ethyl)guanidine; 1-methyl-1-(2-oxo-2-((3S,4R,5S)-3,4,5-trihydroxy-2-(hydroxymethyl)piperidin-1-yl)ethyl)guanidine; 1-methyl-1-(2-oxo-2-((2R,3R,4R,5R)-3,4,5-trihydroxy-2-(hydroxymethyl)piperidin-1-yl)ethyl)guanidine; 1-methyl-1-(2-oxo-2-((2R,3R,5R,6R)-3,4,5-trihydroxy-2,6-bis(hydroxymethyl)piperidin-1-yl)ethyl)guanidine; and 1-methyl-1-(2-oxo-2-((2R,3R,4S,5S,6R)-3,4,5-trihydroxy-2,6-bis(hydroxymethyl)piperidin-1-yl)ethyl)guanidine.

* * * * *